Figure 1:
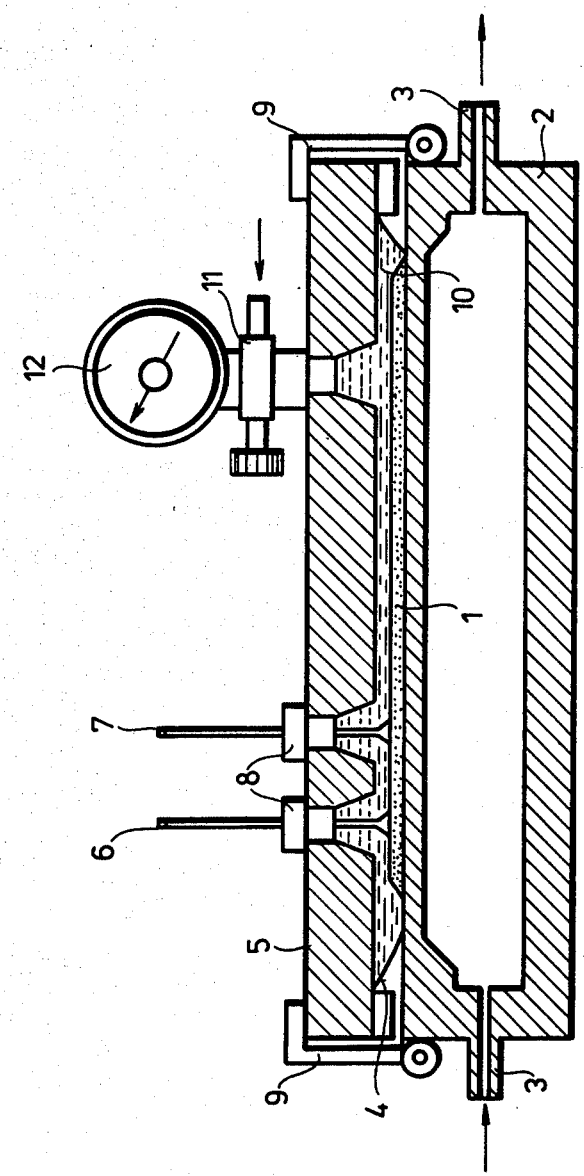

United States Patent [19]

Tyihák et al.

[11] 4,346,001
[45] Aug. 24, 1982

[54] LINEAR OVERPRESSURED THIN-LAYER CHROMATOGRAPHIC APPARATUS

[75] Inventors: Ernö Tyihák, Budapest; Emil Mincsovics, Szentendre; Sándor Diós, Budakalász; Gyula Horváth; Huba Kalász, both of Budapest; János Nagy, Szentendre; Ferenc Körmendi, Budapest; László Kozma, Budapest; János Borsos, Budapest; János Kiss, Budapest, all of Hungary

[73] Assignee: Labor Müszeripari Müvek, Esztergom, Hungary

[21] Appl. No.: 273,209

[22] Filed: Jun. 12, 1981

[51] Int. Cl.³ .............................................. B01D 19/08
[52] U.S. Cl. .................................. 210/198.3; 210/658
[58] Field of Search ................... 210/658, 198.3, 198.2

[56] References Cited

U.S. PATENT DOCUMENTS

| 3,491,883 | 1/1970 | Schaiftman | 210/198.3 |
| 3,553,067 | 1/1971 | Dwyer et al. | 210/198.3 |
| 3,757,952 | 9/1973 | Baitsholts et al. | 210/198.3 |

*Primary Examiner*—John Adee
*Attorney, Agent, or Firm*—Gabriel P. Katona

[57] ABSTRACT

A linear overpressured thin layer chromatographic apparatus comprises a base plate 3 supporting a sorbent layer 1 over which a membrane 4 is filled. The membrane 4 is externally pressurized by a fluid medium 10. A transparent cover plate 5 is fitted over the membrane 4, and there are sealed inlets 6, 7 passing through the cover plate 5 for the introduction of the mobile phase and the samples.

1 Claim, 11 Drawing Figures

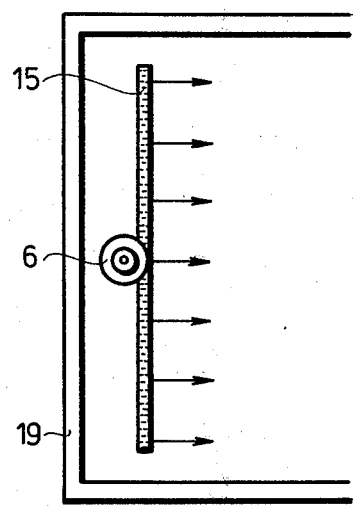
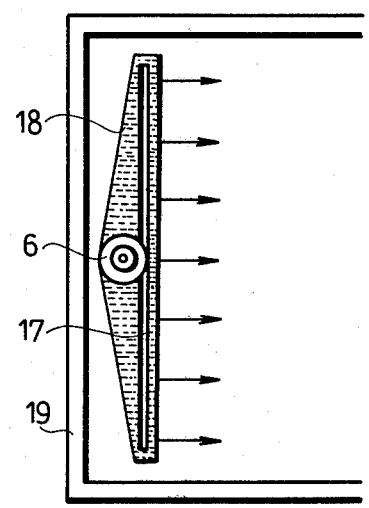
Fig. 2a　　　　　　Fig. 2b
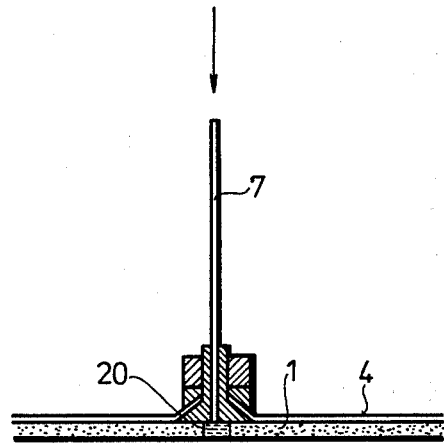
Fig. 3

LINEAR OVERPRESSURED THIN-LAYER CHROMATOGRAPHIC APPARATUS

The invention relates to a linear overpressured thin layer chromatographic apparatus operating with a closed sorbent layer which is pressurised (externally) by a resilient plate by pneumatic, hydraulic or other means, wherein the development temperature can be set to the desired value and the development selected as desired in length or width, one-way or two-way, dry or wet, isocratic or gradient, one-dimensional or two-dimensional, or for the application of the so-called "overrunning" technique.

Overpressured layer chromatography is a closed planar liquid chromatographic technique, wherein the sorbent layer is completely sealed off by a plate put under external pressure and the solvent (mobile phase) is forced to flow among the particles of the sorbent with the aid of a suitable dispenser. (See Hungarian Pat. No. 173,749). This latest embodiment of planar liquid chromatography has several advantages in comparison with "classic" or conventional layer chromatography; short time required for separation, better separation (resolution), low solvent consumption; a possibility of speeding up development by means of viscous solvent mixtures; a possibility of visual evaluation; applicability of aggressive reagents, etc. It may, therefore, be stated that it combines the advantages of overpressured layer chromatography and the high-performance (high velocity, high pressure) column chromatography.

There is, however, only one known embodiment of overpressured thin layer chromatographic apparatus: the so called "annular or circular overpressured chamber" (Tyihák E., Mincsovics E. and Kalász H; J. Chromatog. 174, 75 (1979)) which is characterised in that the apparatus (ultra-microchamber) is made of "plexiglass" and one its plates, the lower plate, receives a max. 200×200 mm, smeared or industrially pre-treated sorbent layer-plate, either after dropping the samples or, in the case of wet running, without sample dropping; then a cover-plate, made of "plexiglass" is placed on the sorbent layer and the following is incorporated thereinto: (a) a manometer, (b) pressurised sample dispenser (c) a gas inlet aperture, (d) an O-ring to clamp the synthetic resin foil, (e) a synthetic membrane and (f) an opening for introducing the solvent by means of a resilient pipe made of metal coil.

The two plates are suitably sealed together and the gas pad or cushion is inflated with nitrogen gas.

A common characteristic of the most widely differing variants known layer chromatographic methods is that the relation between the distance covered by the solvent (z, cm) and the time required for it (t, sec.) can be described by a quadratic equation: $z^2/t=k$, where k is a velocity constant. This also holds true for the liner and circular variants of high-performance liquid chromatography (HPLC), see Kaiser, R. E.: "Einfuehrung in die Hochleistungs-Dünnschicht-Chromatographie"; Institute for Chromatography, Bad-Duerkheim, 1976), as well as for running with overpressurised layer chromatographs of the annular variant (Tyihák et al., J. Chromatog. 174, 75, (1979) since in the latter case it is in principle impossible to ensure constant solvent velocity along the radius of the circle.

A constant solvent velocity, or a linear solvent front are pre-conditions for a satisfactory layer chromatogram but they may only be achieved by a variant of the overpressured linear layer-chromatograph wherein a wire or a platelet for the introduction of a solvent is placed in front of the point of entry of the solvent into the layer which is sealed at its edges or by a channel grooved into the sorbent layer. (Hungarian Patent Application, Dec. 6, 1979. Applicant: Chinoin Rt., Budapest. The title of the patent application is: Chromatographic layer plate for overpressured layer chromatographic apparatus).

In linear overpressured chromatography the relation between the distance covered (migrated) by the solvent (z cm.) and the time required (t sec.) is described by a linear equation: $z/t=k$, where k=velocity constant, thus this variant of overpressured layer chromatography creates conditions similar to those in column chromatographic conditions. This means that as regards quality a new chromatographic technique is presented. It also follows from this that of the two possible variants of overpressured layer chromatography, i.e. the circular and linear embodiments, the development of the latter is to be preferred, or is more justified, because it is there that an advance on the present state of art in respect of a more efficient separation can be expected.

Thus, the practical realization of overpressured linear layer chromatography requires suitably developed special sorbent plates, (see Chinoin Rt. Budapest, Hungarian Patent Application of Dec. 6, 1979) and apparatus (chamber).

In the light of the published values of running time the further-developed linear apparatus, based on Hungarian Patent No. 173.749, (Tyihák and others, J. Chromatog. 191,293 (1980)) can only be used for runs over relatively short distances, although it follows from the basic law of the linear technique embodied in a linear equation ($k=z/t$) that the flow velocity of the solvent remains constant also over longer distances. Since as is known, the theoretical "plate-number" or "separation-number" introduced by Kaiser (Kaiser, R. E., Editor "Einfuehrung in die Hochleistungs-Dünnschicht-Chromatographie", Bad Duerkheim, 1976) increases proportionally with the distance of the run, and so over longer distances (e.g. 30–100 cm) more efficient resolution than hitherto should be achievable.

It follows from the principle of overpressured layer chromatography that the chromatographic operations take place under the exclusion of solvent vapours similarly to column chromatography using dry packing. This frequently leads to the de-mixing or separation-out of solvents from multicomponent solvent mixtures and therefore in liquid-solid (adsorption) overpressured layer chromatography to imperfect separation and to congestion or agglomeration of the materials to be separated at the boundaries of the separation zone. In such cases the disadvantageous separation could be counteracted by preconditioning with the solvent used with the sorbent, as in high-performance column chromatography. This kind of linear apparatus is, however, not known at the present. The evolution and application of a linear apparatus, which is also suitable for wet runs is further justified by the existing need for modelling high-performance column-chromatography and by the requirement for the simultaneous application of the two techniques for analytical and/or preparative purposes.

An aim of the invention is to eliminate the drawbacks described above and to satisfy the practical demand for a linear overpressured layer chromatograph suitable for the development of a closed, pneumatically, hydraulically or otherwise pressurised sorbent-layer which can be set to any desired, which is discretionally selectable to be long or wide, undirectional or bidirectional dry or wet, isocratic or gradient, one-dimensional or two-dimensional and applicable to the so-called "over-running" technique.

The invention is based on the theoretically founded discovery that in linear overpressured thin layer chromatography the flow rate of the solvent remains constant over the full length of the layer, therefore runs over longer distances is justified and results in substantially more efficient separation than hitherto.

The invention is based on the recognition that the detrimental consequences of the separation or de-mixing into components of the solvent-mixture are eliminated analogously to high-performance column chromatography by preconditioning with a solvent, by dispensing or feeding the samples under pressure or after removal of the pressure. This is also the basis of the modelling of high-performance column-chromatographic separation. Furthermore, the invention is based on the recognition that the application of a sorbent layer with sealed or boundaries edges if so required, renders one or two-way running possible by using inlet apertures for the solvent built into the linear over-pressured layer chromatograph for variable operation according to the actual requirements.

Finally, the invention is based on the recognition that by setting the temperature of the sorbent-layer in the apparatus to a lower or higher degree than normal, better separation can be achieved than hitherto.

The solution according to the invention is, therefore, embodied in a linear overpressured layer-chromatographic apparatus (chamber), which is suitable for the application of discretionally selectably long or wide, one-way or two-way, dry or wet, isocratic and gradient, one-dimensional or two-dimensional development or for the so called "over-running" technique and, at the same time, ensures the possibility of setting the temperature of the sorbent layer plate or running. The essence of the invention is that it utilizes the theoretically proved interrelation between the plate number, the separation-number and the distance of the solvent migration in order to build apparatus suitable also for long runs as well as building into the apparatus a variable system of solvent introductions for wet elution, and a similarly variable sample dispensing system ensuring the possibility of a discretional selection of application. It is also an important feature of the invention that by means of a built-in temperature control the temperature of the solvent and of the elution can be regulated.

According to the invention, a linear overpressured layer-chromatographic apparatus comprises:
1. A base plate, the dimensions of which are selected to suit the requirements of the new method regarding maintenance and control of the temperature of the sorbent layer plates;
2. A transparent, resilient damping plate which is provided with a gas cushion and is suitable for pressing down the sorbent layer, and the material of which is chemically resistant to solvents;
3. Capillary connectors for the introduction of eluents and samples.

Figure 2:
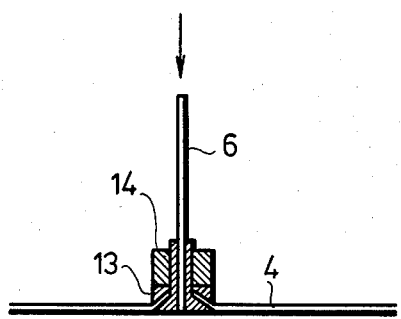
Figure 2C:
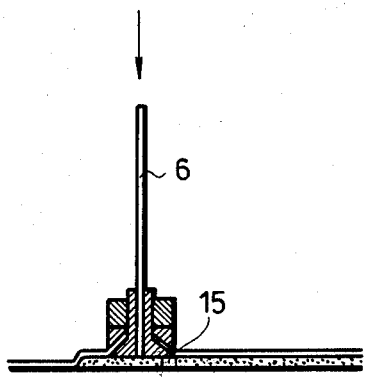
Figure 2D:
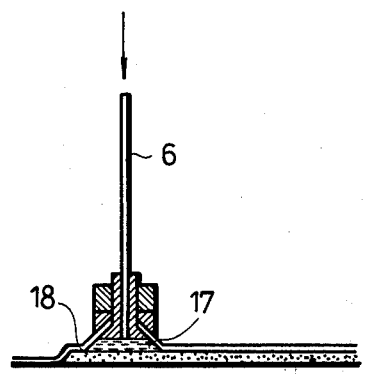
Figure 4A:
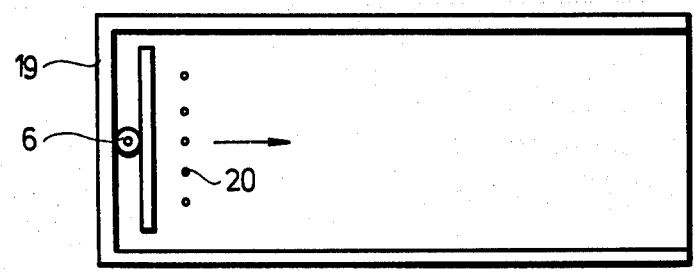

The invention is further described purely by way of preferred embodiments illustrated in the accompanying drawings, wherein:

FIG. 1 is a cross-section of the apparatus according to the invention,

FIG. 2 is a cross-section of capillary connecting pieces for the introduction of eluents, FIGS. 2a and 2b are respective plan views of further embodiments of the capillary connection pieces for the introduction of eluents, with FIGS. 2c and 2d showing the capillary connection pieces of FIGS. 2a and 2b, respectively in cross-section, FIG. 3 is a cross-section of the sample dispenser, FIGS. 4a, b, c and d illustrate various methods for the introduction of eluents and samples.

In FIG. 1 a sorbent layer plate 1 is located on a thermostatically controlled base plate 2. Nipples 3 can be connected to ultra-thermostats to provide the temperature required for the chromatographic operation.

A membrane 4 for the clamping plate of the sorbent-layer is fastened to a strong, transparent synthetic resins or glass plate 5. Capillary inlet connectors 6 and 7, respectively for eluents and for samples are connected to the membrane 4. The capillary connectors project to the external space or surroundings via seals 8 in the transparent strong plate 5.

The base plate 2 and the clamping plate 5 are tightly clamped together by means of a special closure 9. A high-pressure liquid or gaseous phase 10 is introduced between the membrane 4 and the transparent plate 5 via a valve 11. A manometer 12 indicates the prevailing pressure conditions. The sorbent layer plate 1 is directly sealed by the pressure exerted by the elastic pad or cushion developed on one side of the clamping plate 5. The degree of clamping depends on the magnitude of the pressure applied.

The seals 8 of the capillary inlet connectors permit movement of membrane 4 and/or of the capillary connectors 6, 7 in such a way that the fluid-tightness of the space 10 under pressure is assured.

As shown in FIG. 2, the capillary connector 6 for the introduction of the mobile phase is connected to the membrane 4 by means of a conical seal. The tightness of this seal is ensured by means of a conical shim 13 and a threaded nut 14. The mobile phase may be introduced via a channel 15 formed in the sorbent layer, or via a channel 18 formed by the spacing wire 17 placed on the sorbent layer, the plate strip and the clamped membrane 4 (FIGS. 2a to 2d).

Initially the channel 15 and the sorbent layer 1 behind it fill up. Thereafter, as the pressure increases, linear flow indicated by arrows is set up in the sorbent layer, the edges of which are sealed by impregnation 19.

In FIG. 3 the capillary connector 7 for the introduction of samples is laid directly on the sorbent layer 1. The sample 20 flows into the sorbent-layer 1 by overpressure. The sample can be introduced by wetting the sorbent layer by the flow of the eluent, or without wetting into a dry sorbent-layer. The magnitude of the overpressure for the sample dispensing is determined by the magnitude of the pressure in the cushion 10 which presses down the sorbent-layer 1, by the particle size of the sorbent and by the viscosity conditions.

Figure 4B:
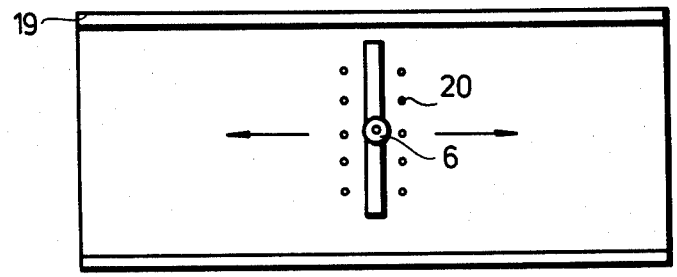

FIGS. 4a to 4d show various embodiments of the eluent and sample-taking in the linear overpressured layer chromatographic apparatus, according to the invention, offering the possibility of the realization of different ways of separation:

a. One-way runs with pre-loaded samples. The mobile phase is introduced through the capillary connector 6 via the channel 15 and sets the components of the pre-loaded samples 20 into a one-way linear motion (FIG. 4a).

b. Two-way runs with pre-loaded samples. The phase or eluent is introduced through the capillary connector 6 via the channel 15 and sets the greater number of pre-loaded samples 20 arranged in two rows into a two-way (bidirectional) linear motion (FIG. 4b).

c. One-way running with pressurized sample dispensing.

Figure 4C:
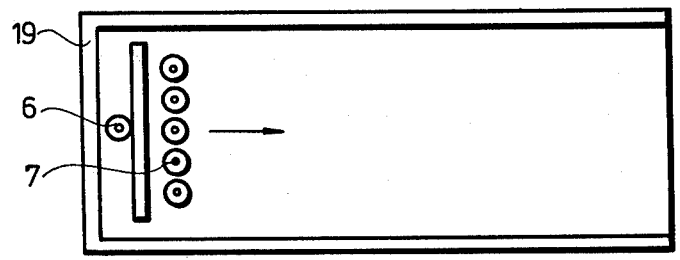
Figure 4D:
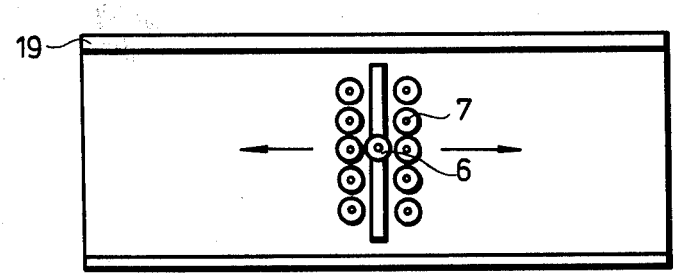

The eluent is introduced through the capillary connector 6 via the channel 15 and wets or elutriates the sorbent-layer. The samples are introduced through the capillary connector 7. The flow of eluent sets the samples into a one-way (unidirectional) linear motion. (FIG. 4c).

d. Two-way (bidirectional) running with pressurized sample dispensing. The elutriates the sorbent-layer via the channel 15 in two directions. Through a greater number of capillary connectors 7 arranged in two rows a plurality of samples are introduced. The flow of the eluent sets the samples into a bidirectional linear motion. (FIG. 4d).

The front of the eluent can be observed through the transparent clamping plate. In the case of a coloured compound or mixture the motion of the sample may be observed directly. In the case of a colourless sample coloured tracing additives may be used to make the visual observation possible.

The evaluation of the separation is carried out with the aid of the methods used in traditional layer chromatography.

We claim:

1. Linear overpressured layer chromatographic apparatus comprising a base plate to support a sorbent layer, a cover plate fastenable to the base plate and fitted with a membrane for resiliently clamping down the sorbent layer, means for controlling the introduction of a pressurising between the cover plate and the membrane; and the cover plate is provided with at least one inlet for the mobile phase and at least one sample inlet sealedly passed through the membrane plate.

* * * * *